United States Patent [19]
Brock-Fisher

[11] Patent Number: 6,077,225
[45] Date of Patent: Jun. 20, 2000

[54] ULTRASOUND METHOD FOR ENHANCING IMAGE PRESENTATION WHEN CONTRAST AGENTS ARE USED

[75] Inventor: George A. Brock-Fisher, Andover, Mass.

[73] Assignee: Hewlett-Packard Company, Palo Alto, Calif.

[21] Appl. No.: 09/012,291

[22] Filed: Jan. 23, 1998

[51] Int. Cl.$^7$ .............................. A61B 8/00; A61H 1/00
[52] U.S. Cl. .............................................. 600/439; 601/2
[58] Field of Search .................................... 600/437, 439, 600/440, 441, 454, 458; 601/2

[56] References Cited

U.S. PATENT DOCUMENTS

| | | | |
|---|---|---|---|
| 5,040,537 | 8/1991 | Katakura | 600/300 |
| 5,542,935 | 8/1996 | Unger et al. | 600/458 |
| 5,558,092 | 9/1996 | Unger et al. | 600/439 |
| 5,577,505 | 11/1996 | Brock-Fisher et al. | 600/458 |
| 5,735,281 | 4/1998 | Rafter et al. | 600/458 |
| 5,762,066 | 6/1998 | Law et al. | 600/439 |
| 5,776,063 | 7/1998 | Dittrich et al. | 600/458 |
| 5,833,613 | 11/1998 | Averkiou et al. | 600/440 |
| 5,833,615 | 11/1998 | Wu et al. | 600/458 |
| 5,860,931 | 1/1999 | Chandler | 600/458 |
| 5,873,829 | 2/1999 | Kamiyama et al. | 600/458 |

OTHER PUBLICATIONS

Porter et al., "Transient Myocardial Contrast After Initial Exposure to Diagnostic Ultrasound Pressures with Minute Doses of Intravenously Injected Microbubbles", Circulation, vol. 92, (1995), pp. 2391–2395.

*Primary Examiner*—Marvin M. Lateef
*Assistant Examiner*—Ali M. Imam

[57] ABSTRACT

Improved ultrasound images of a patient's tissue region of interest (ROI) are achieved through the use of a contrast agent. The method includes the steps of: administering the contrast agent to the patient's circulatory system; providing a user interface which enables a user to select a target region within the tissue ROI to be irradiated and to operate an ultrasound transducer to irradiate the selected target region with sufficient ultrasound energy to substantially reduce a backscatter effect of contrast agent that is present therein; and operating an ultrasound transducer to image the tissue ROI. It is preferred that the contrast agent be encapsulated into microbubbles The method is further applicable to selective destruction of encapsulated therapeutics which arrive at a tissue ROI to which the therapeutic is to be administered.

16 Claims, 2 Drawing Sheets

ULTRASOUND METHOD FOR ENHANCING IMAGE PRESENTATION WHEN CONTRAST AGENTS ARE USED

FIELD OF THE INVENTION

This invention relates to ultrasound imaging and, more particularly, to use of encapsulated contrast and therapeutic agents in combination with ultrasound imaging apparatus.

BACKGROUND OF THE INVENTION

Current research activities employ contrast-enhancing agents in conjunction with ultrasound imaging to improve the visualization of the perfusion of internal organs. The contrast agents are often configured as microbubbles that comprise a shell which acts to contain an internal gas or other contrast enhancing agent. For instance, perfluorocarbon-exposed sonicated dextrose albumin microbubbles have been employed to improve the contrast of ultrasound images. Typically, these microbubbles can be destroyed if sufficiently high levels of ultrasonic energy are applied.

One disadvantage of utilizing such contrast-enhancing agents is that the scattering of acoustic energy which results from their presence causes a reduction of transmitted acoustic energy therethrough. As a result, structures that lie distally to an area that has been perfused with a microencapsulated contrast agent are "shadowed" by the contrast enhancing agent. For instance, when such a contrast agent is administered to the heart, while attempting to image the perfusion of the arterial structures of the myocardium, the left ventricle blood pool will substantially shadow the distally located myocardial wall structure.

Porter et al. have reported upon use of a transient imaging technique which utilizes contrast enhancing microbubble agents. See: "Transient Myocardial Contrast After Initial Exposure to Diagnostic Ultrasound Pressures with Minute Doses of Intravenously Injected Microbubbles", Circulation, Volume 92, (1995), pages 2391–2395. In particular, Porter et al. administered contrast enhancing microbubbles to the hearts of dogs and then subsequently measured myocardial contrast during triggered ultrasound imaging cycles (i.e., one scan per cardiac cycle). Further, they withheld real-time ultrasound transmission until after microbubbles had entered the myocardium, after intravenous injection.

Porter et al. reported that the transient imaging produced significantly greater myocardial contrast than continuous imaging. One rationale presented for the improved imaging was that the standard-imaging pulse rates destroyed the microbubbles. By delaying ultrasound transmission or triggering pulses to one part of the cardiac cycle, more bubbles were enabled to reach the myocardium and hence caused greater contrast.

In utilizing encapsulated contrast agents, it would be useful to cause destruction of the microbubbles (and thus a significant reduction in the ultrasound shadowing effect created thereby) by selectively timing destruction of the microbubbles so as to enable subsequent imaging of distally located regions which also contain the contrast agent microbubbles.

In addition to the use of contrast agent microbubbles, investigators have proposed the encapsulation of a therapeutic into microbubbles. To assure enhanced effectiveness of the encapsulated therapeutic, it would be useful to have a method for causing release of the therapeutic from the microbubbles at a target site.

SUMMARY OF THE INVENTION

Improved ultrasound images of a patient's tissue region of interest (ROI) are achieved through the use of a contrast agent. The method includes the steps of: administering the contrast agent to the patient's circulatory system; providing a user interface which enables a user to select a target region within the tissue ROI to be irradiated and to operate an ultrasound transducer to irradiate the selected target region with sufficient ultrasound energy to substantially reduce a backscatter effect of contrast agent that is present therein; and operating an ultrasound transducer to image the tissue ROI. It is preferred that the contrast agent be encapsulated into microbubbles The method is further applicable to selective destruction of encapsulated therapeutics which arrive at a tissue ROI to which the therapeutic is to be administered.

DETAILED DESCRIPTION OF THE PREFERRED EMBODIMENT

An ultrasound system embodying the invention makes use of the fact that ultrasound energy can destroy, or substantially modify, the contrast enhancing ability of a contrast agent. More specifically, when the contrast agent is encapsulated in microcapsules, application of sufficiently high levels of ultrasound energy can cause a rupture of the capsule walls and diffusion of the contrast agent. As a result, the effectiveness of the contrast agent is greatly, if not entirely, dissipated.

A preferred embodiment of the invention employs a pair of ultrasonic transducers which are configured in such a manner as to be able to image one or more planes at the same time. One of the planes is termed the "investigational" plane and the other is termed the "control" plane. The transducer producing the investigational plane image is placed by the operator so as to maximize visualization of the tissue ROI. The transducer producing the control plane is placed so as to intersect a blood path which supplies the tissue ROI. Next, the contrast agent is introduced into the blood stream, either by bolus or by an infusion injection.

After the contrast agent has perfused the tissue ROI, the control plane transducer is activated to scan a region through which the contrast agent passes. The control plane is scanned with sufficient acoustic power so as to destroy the effectiveness of the contrast agent present therein. As an example, the investigational plane can be placed in the parasternal long-axis or apical four-chamber view of the heart to investigate myocardial perfusion. The control plane can be placed along the short axis view of the heart, directly at the mitral valve so as destroy the contrast agent as it enters the left ventricle, thereby eliminating the shadowing effect that would occur if the contrast agent was allowed to enter therein.

The operation of the system occurs as follows. The investigational and control transducers are positioned as described above and the contrast agent is introduced into the blood stream. During a first cardiac cycle, the contrast agent is ejected from the left ventricle and finds its way into the arterial pathways within the myocardium. Immediately after ejection of the contrast agent from the left ventricle, the control transducer is turned on and thereafter destroys encapsulated contrast agent which passes through the mitral valve and into the left ventricle. Prior to a next ejection from the left ventricle, an investigational ultrasound scan is taken of the myocardium. Since the contrast agent microbubbles entering the left ventricle have been largely destroyed—and their its contrast enhancing effectiveness substantially reduced, the shadowing effect is avoided that otherwise would have been present had the microbubbles been allowed to enter the left ventricle.

Figure 1:
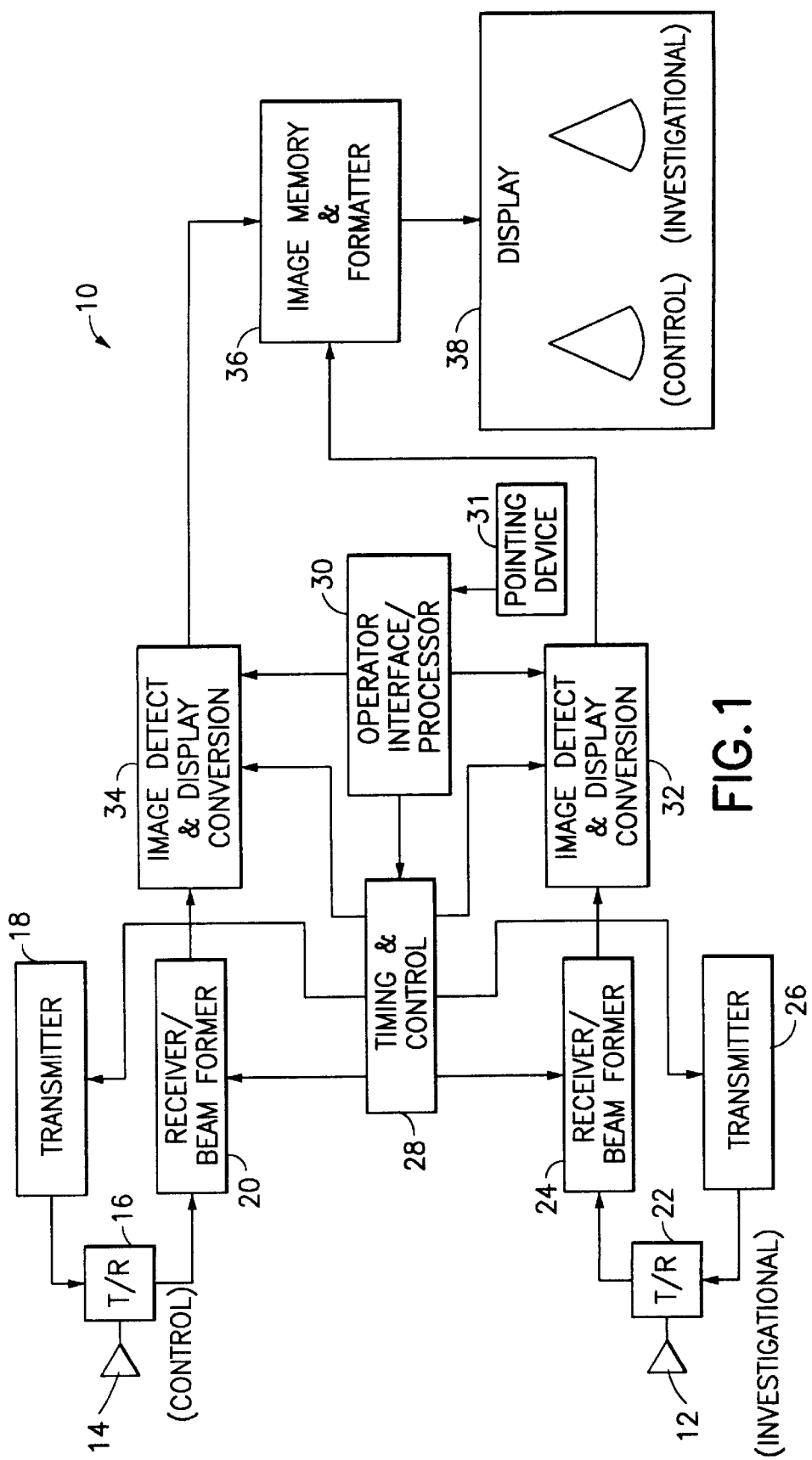
FIG. 1 is a block diagram of an ultrasound imaging system that embodies the invention.

Turning now to FIG. 1, an ultrasound imaging system 10 is illustrated that is particularly adapted to carrying out the method of the invention. Investigational ultrasound transducer 12 is designed to provide diagnostic images of a desired tissue ROI. Control ultrasound transducer 14, is principally used to provide acoustic power of sufficient intensity to selectively destroy contrast agent-containing microbubbles. Both transducers 12 and 14 are capable of providing real-time, two dimensional images of internal body organs, however, control transducer 14 is optimized to provide high power levels, while investigational transducer 12 is optimized to provide superior image quality.

Control transducer 12 is associated with a transmit/receive module 16, a transmitter 18 and a receiver/beam former 20. In a similar manner, investigational transducer 12 is associated with a transmit/receive module 22, a transmitter 24 and a receiver/beam former 26. The timing of the respective transmitters/receiver-beam formers is controlled by signals from timing and control module 16 which is, in turn, controlled by a processor 30. Input controls to processor 30 are entered via a pointing device, such as a mouse or trackball 31.

Timing and control module 28 further controls outputs from receiver/beam formers 20 and 24 as they are applied to respectively connected image detection/display conversion modules 32 and 34. Within the aforesaid modules, the received ultrasound signals are converted into images which are stored in image memory and formatter 36. Thereafter, processor 30 causes the respectively stored images to be presented on display 38. It is to be understood that the operation of ultrasound imaging system 10 is otherwise conventional and requires no further detailed explanation.

Note that investigational transducer 12 and control transducer 14 can both provide ultrasound images to display 39. However, the images from control transducer 14 are mainly utilized to enable a proper positioning of the control plane so as to enable destruction of contrast agent microcapsules as they are about to enter a region which shadows a tissue ROI that is to be imaged by investigational transducer 12.

Figure 2:
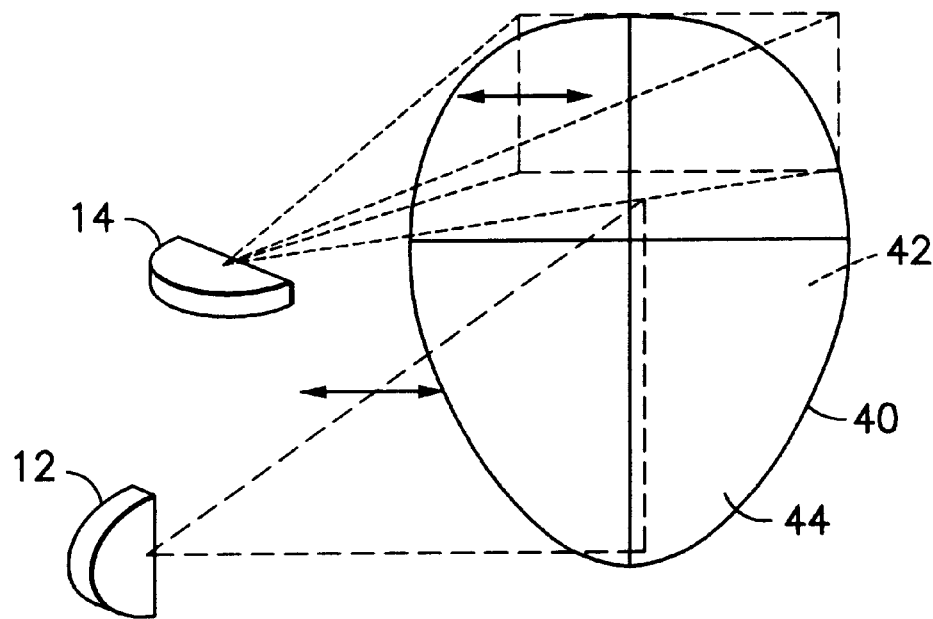
FIG. 2 is a first embodiment of the invention illustrating the placement of a pair of ultrasound transducers in relation to a heart.

FIG. 2 illustrates the positioning of investigational transducer 12 and control transducer 14 with respect to a heart 40. As will be recalled, an object of the invention is to enable ultrasonic imaging of, for instance, myocardium 42 which lies distally behind left ventricle 44 of heart 40 (with respect to investigational transducer 12). Utilizing the illustrated arrangement of investigational transducer 12 and control transducer 14, an examination of a patient will proceed as follows: Investigational transducer 12 is positioned on the patient so as to provide a view of the tissue ROI. For example, investigational transducer 12 is positioned to provide a parasternal long-axis view of heart 40. Control transducer 14 is then positioned in such a manner as to destroy contrast agent microbubbles entering a chamber of the heart, i.e., left ventricle 44. Accordingly, control transducer 14 is positioned to image the parasternal short axis view which intersects the lumen of the mitral valve (not shown) of heart 40. The imaging capability of control transducer 14 is utilized to enable precise positioning of the control plane.

After transducers 12 and 14 are positioned as above-described, a suitable contrast agent, such as perfluorocarbon microbubbles, is intravenously injected into the patient's circulatory system. As the contrast agent flows into left ventricle 44, a subsequent cardiac cycle causes ejection of the contrast agent into the arterial pathways of myocardium 42. Prior to a next cardiac cycle, control transducer 14 is energized and is caused to scan the mitral valve region with a beam of high energy ultrasound signals. Such signals destroy the contrast agent microbubbles passing through the mitral valve and into left ventricle 44.

Images obtained from investigational transducer 12 can then be examined, on a frame-by-frame basis, both when contrast agent microbubbles are present in ventricle 44 and when not present, so as to determine the perfusion of myocardium 42 or other clinically significant aspects.

Figure 3:
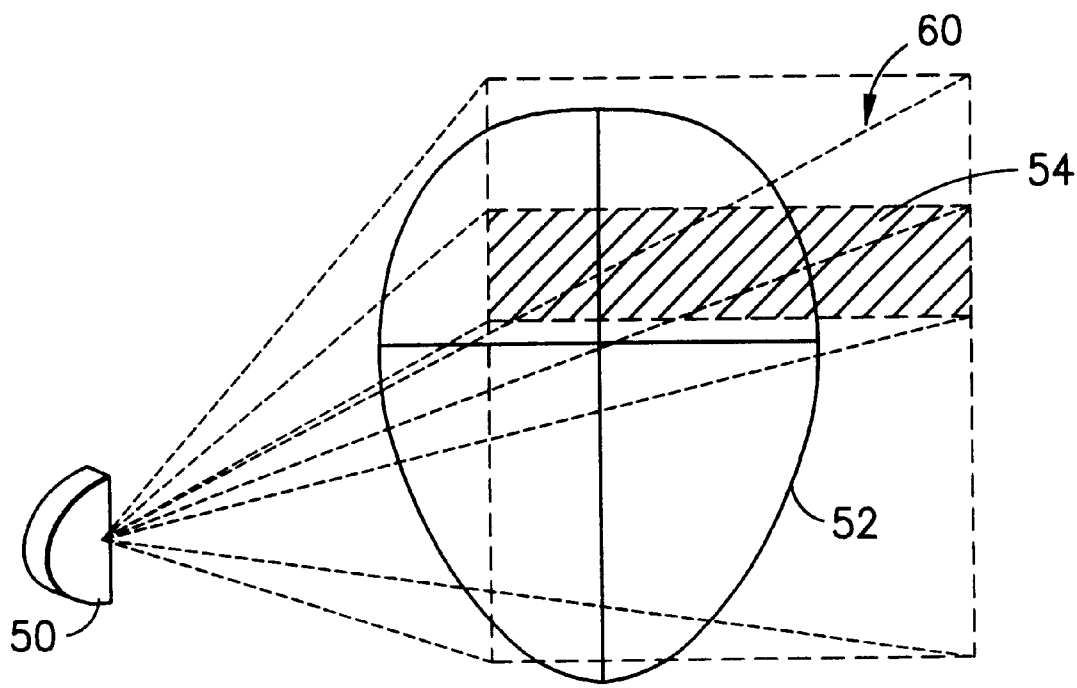
FIG. 3 illustrates a second embodiment of the invention wherein only one transducer is employed during operation of the invention.

While the preferred embodiment of the invention employs a pair of ultrasound transducers, the invention can be applied to an ultrasound imaging system wherein both the control and investigational functions are performed by a single transducer. FIG. 3 illustrates such a system wherein ultrasound transducer 50 is positioned to provide a parasternal long-access view of heart 52. When such a single transducer is employed (refer back to FIG. 1), ultrasound system 10 is modified by eliminating, for instance, control transducer 14 and its associated transmitter/receive signal paths, etc.

Accordingly, for the embodiment of FIG. 3, transducer 50 is substituted for transducer 12 and is utilized for both investigational imaging and for generation of the control, high power, contrast agent destruction signals. Such operation initially utilizes transducer 50 to image heart 52 using the long axis parasternal plane in a normal investigational manner. The user, by control of pointing device 31 then outlines a region 54 of heart 52 which is to be scanned by the high power ultrasound signals. This action enables pixel coordinates defining region 54 to be acquired by processor 30, which coordinates are thereafter utilized in the control of timing and control module 32.

More specifically, when it is determined that scanned beam 60 enters region 54 (determined from the entered coordinate values), a power change signal is dispatched to transmitter 26 which, in turn, causes transmit/receive module 22 to apply higher power ultrasound signals to transducer 50. Thus, a higher power ultrasound beam is scanned across region 54 and destroys contrast agent microbubbles that are present therein. As a result, the contrast microbubbles are prevented from entering the left ventricle of heart 52 and the remaining scan of the region occurs without the shadow effect which would result if the microbubbles were present. Thus, when the investigational beam is caused to image the region of the ultrasound beam lying below area 54, identical results are obtained as with the dual transducer arrangement.

It is to be understood that while the above description assumes that both the high power control and lower power investigational actions take place during a single scan, such actions can be controlled to occur during succeeding scans or in any other sequence which prevents a shadowing of a tissue ROI.

The invention can also be applied to a study of "wash-in and wash-out" actions in a target region. More specifically, if a microencapsulated contrast agent is injected into a patient's circulatory system, control transducer 14 (or transducer 50) can be positioned by the user so as to scan the target region where a wash-in action is to be observed. Then, after the encapsulated contrast agent is injected and perfuses the target region of interest, the control transducer is energized to cause a rupture of the microbubbles therein. Then, transducer 12 (or transducer 50) is energized to produce multiple time lapse images of the region of interest to determine how long it takes for the microbubbles to reappear therein. In a wash out study, once the target region has been perfused with microbubbles, the control transducer is positioned to destroy microbubbles that thereafter enter the target region. When succeeding images are acquired, the time required can be determined for the microbubbles to wash out of the target region.

It is to be understood, that the invention can also be applied when other than contrast agent microbubbles are administered to a patient's circulatory system. More specifically, if a microencapsulated therapeutic is injected into a patient's circulatory system, control transducer 14 (or transducer 50) can be positioned so as to scan a target region of tissue to which the therapeutic is to be administered. Then, when encapsulated therapeutic is injected, the control transducer is energized to cause a rupture of the microbubbles when they enter the target region. Accordingly, the therapeutic is released directly in the region to be treated.

To achieve additional restriction of the area wherein the therapeutic-containing microbubbles are destroyed, plural transducers with angularly oriented, overlapping and intersecting beam scan patterns can be used. (See for instance FIG. 2 wherein the horizontal beam pattern from transducer 14 is lowered to intersect the vertical beam pattern of transduce 12 at a region where the therapeutic is to be released). Then, by adjusting the beam powers such that only where the beams intersect is there sufficient power (derived from both beams) to rupture the microbubbles, a restricted release region is created.

It should be understood that the foregoing description is only illustrative of the invention. Various alternatives and modifications can be devised by those skilled in the art without departing from the invention. Thus, while encapsulated contrast agents have been described above, other non-encapsulated contrast agents are equally usable. For example, a fluorocarbon contrast agent which boils (and creates bubbles as a result) at body temperature is equally usable as the applied ultrasound contrast agent as its microbubbles will be similarly affected by the incident ultrasound signals. Accordingly, the present invention is intended to embrace all such alternatives, modifications and variances which fall within the scope of the appended claims.

What is claimed is:

1. A method for providing improved ultrasound images of perfusion of a patient's tissue region of interest (ROI) through use of a contrast agent, wherein said tissue ROI is positioned so that ultrasound reflections received by an imaging transducer are affected by an obscuring region that is perfused with said contrast agent, said method comprising the steps of:

a) administering said contrast agent to said patient's circulatory system so that said contrast agent reaches both said obscuring region and said tissue ROI;

b) controlling said ultrasound transducer means to irradiate said contrast agent that enters said obscuring region, with sufficient ultrasound energy to substantially reduce an effect of said contrast agent upon ultrasound transmissions through said obscuring region; and c) operating said ultrasound transducer means to image said tissue ROI.

2. The method as recited in claim 1, wherein said contrast agent is encapsulated and said ultrasound energy from said ultrasound transducer means is sufficiently strong to rupture structures which encapsulate said contrast agent.

3. The method as recited in claim 1, wherein said ultrasound means comprises a first ultrasound transducer and a second ultrasound transducer, and wherein step b) controls said first ultrasound transducer to image said tissue ROI and controls said second ultrasound transducer to provide sufficient radiation energy to reduce said effect of said contrast agent.

4. The method as recited in claim 3, wherein said second ultrasound means is controlled to position said radiation energy so as not to affect contrast agent which is present in said tissue ROI.

5. The method as recited in claim 4, wherein step c) operates, at nonsimultaneous times, said first ultrasound transducer to image said tissue ROI and said second ultrasound transducer to reduce said effect of said contrast agent, so as to enable observation of flow of said contrast agent into and through said tissue ROI.

6. The method as recited in claim 4, wherein said first ultrasound transducer images said tissue ROI using a first scan plane and said second ultrasound transducer provides said radiation energy in a second scan plane, wherein said second scan plane is non-coplanar with said first scan plane.

7. The method as recited in claim 2, wherein said tissue ROI includes a region of a patient's heart muscle and said subregion is positioned to enable rupture of said encapsulated contrast agent as it enters a ventricle of said patient's heart.

8. An ultrasound method for controlling administration of an encapsulated therapeutic agent to a patient's tissue region of interest (ROI), said method comprising the steps of:

a) administering said encapsulated therapeutic agent to said patient so that said encapsulated therapeutic agent reaches said tissue ROI; and b) operating imaging transducer means (i) to image said tissue ROI, and (ii) to radiate said encapsulated therapeutic agent only within a selected subregion of said tissue ROI that is imaged, with sufficient ultrasound energy to cause a release said therapeutic agent.

9. The ultrasound method as recited in claim 8, wherein said radiation from said ultrasound transducer means is sufficiently energetic to rupture structures which encapsulate said therapeutic agent.

10. The method as recited in claim 8, wherein said ultrasound means comprises a first ultrasound transducer and a second ultrasound transducer that are oriented so that beam patterns produced thereby intersect at said tissue ROI, and wherein step b) operates said first ultrasound transducer and said second ultrasound transducer to provide sufficient radiation energy to cause said release of said therapeutic agent only at a region of intersection of said beam patterns.

11. The method as recited in claim 8, wherein said ultrasound means comprises a first ultrasound transducer and a second ultrasound transducer, and wherein step b) operates said first ultrasound transducer to image said tissue ROI and operates said second ultrasound transducer to provide sufficient radiation energy to cause said release of said therapeutic agent.

12. The ultrasound method as recited in claim 8, wherein said encapsulated therapeutic agent also includes an ultrasound contrast enhancing agent.

13. An ultrasound apparatus for enabling control of administration of an encapsulated therapeutic agent to a patient's tissue region of interest (ROI) when said encapsulated therapeutic agent reaches said tissue ROI, said ultrasound apparatus comprising:
   a) means for operating transducer means to image said tissue ROI; and
   b) means for controlling said transducer means to radiate said encapsulated therapeutic agent only within a selected subregion of said tissue ROI that is imaged, with sufficient ultrasound energy to cause a release said therapeutic agent.

14. The ultrasound apparatus as recited in claim 13, wherein said radiation from said ultrasound transducer means is sufficiently energetic to rupture structures which encapsulate said therapeutic agent.

15. The ultrasound apparatus as recited in claim 13, wherein said ultrasound means comprises a first ultrasound transducer and a second ultrasound transducer that are oriented so that beam patterns produced thereby intersect at said tissue ROI, and wherein means b) operates said first ultrasound transducer and said second ultrasound transducer to provide sufficient radiation energy to cause said release of said therapeutic agent only at a region of intersection of said beam patterns.

16. The ultrasound apparatus as recited in claim 13, wherein said ultrasound means comprises a first ultrasound transducer and a second ultrasound transducer, and wherein means b) operates said first ultrasound transducer to image said tissue ROI and operates said second ultrasound transducer to provide sufficient radiation energy to cause said release of said therapeutic agent.

* * * * *